United States Patent [19]

Farber

[11] 4,016,174
[45] Apr. 5, 1977

[54] BENZOINDOLE PHTHALIDES
[75] Inventor: Sheldon Farber, Appleton, Wis.
[73] Assignee: NCR Corporation, Dayton, Ohio
[22] Filed: Apr. 10, 1975
[21] Appl. No.: 566,854
[52] U.S. Cl. ............... 260/326.14 R; 260/250 BC; 260/295 T
[51] Int. Cl.² ..................................... C07D 405/04
[58] Field of Search ............................. 260/326.14

[56] References Cited
UNITED STATES PATENTS 3,736,337  5/1973  Farber .......................... 260/343.3

Primary Examiner—Donald G. Daus
Assistant Examiner—Jose Tovar
Attorney, Agent, or Firm—E. Frank McKinney

[57] ABSTRACT

A chromogenic compound of normally colorless form is disclosed having the following structural formula:

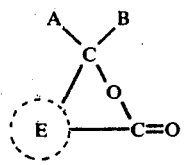

wherein A can be aminophenyl, indolyl, and benzoindolyl, substituted or not;
B can be benzoindolyl, substituted or not; and E can be a broad family of aromatic and heterocyclic structures. The compound is eligible for use in pressure-sensitive record materials and manifold marking systems. Because of light absorption characteristics, selected compounds of this invention are especially useful where broad spectrum absorption and machine readability are important.

4 Claims, 1 Drawing Figure (I) 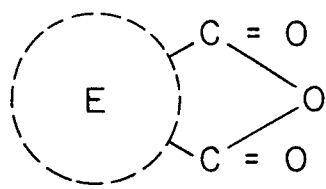
(A) 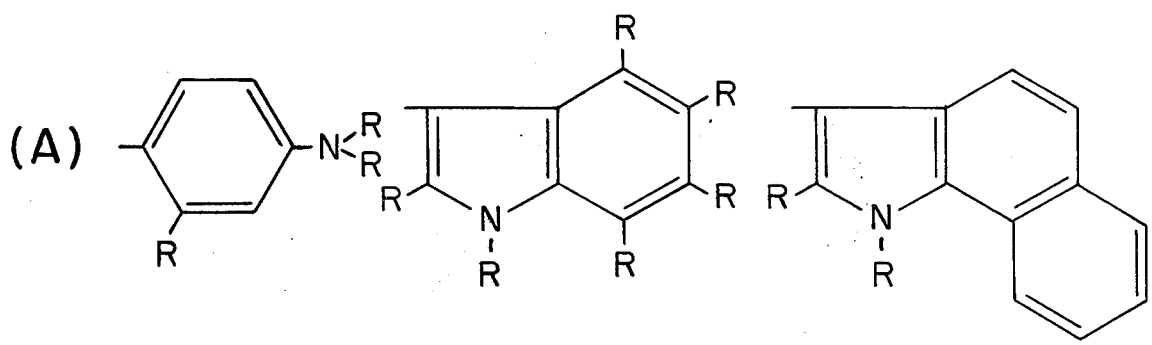
(II) 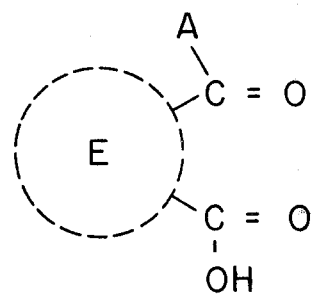
(B) 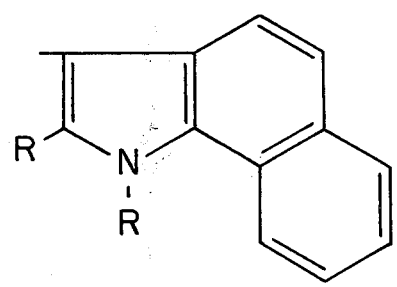
(III) 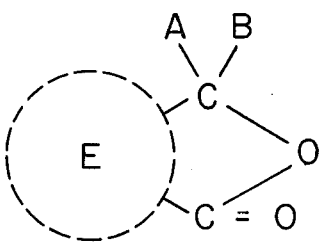

BENZOINDOLE PHTHALIDES

BACKGROUND OF THE INVENTION

1. Field of the Invention

This invention pertains to colorable chromogenic compounds eligible for use in pressure-sensitive record material. Pressure-sensitive mark-forming record systems, single sheet and manifold, are improved by use of these compounds.

More specifically, this invention relates to chromogenic compounds having at least one benzoindolyl moiety which compounds have the form of substantially colorless or slightly colored solids, or which approach being colorless when in liquid solution; but, which may be converted to dark-colored forms upon reactive contact with acidic material. As used in mark-forming systems, marking in desired areas on support webs or sheets may be accomplished by effecting localized reactive contact between the chromogenic material and the acidic material on or in such web or sheet, such material being brought thereto by transfer, or originally there in situ, the desired reactive contact forming dark-colored materials in the intended image-marking areas.

The chromogenic compounds of this invention have the following general formula:

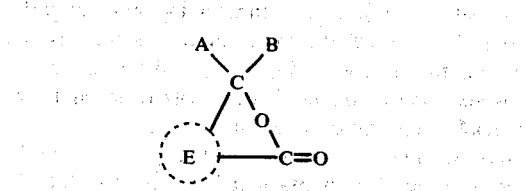

wherein A can be aminophenyl, indolyl, and benzoindolyl, substituted or not; B can be benzoindolyl, substituted or not; and E can be a broad family of aromatic and heterocyclic structures.

2. Description of the Prior Art

Several phthalide and fluoran chromogenic compounds have been disclosed. For example, U.S. Pat. Nos. 3,491,111, and 3,491,116, issued Jan. 20, 1970, disclose indole- and carbazol-substituted phthalides. U.S. Pat. No. 2,417,897, issued Mar. 25, 1947, discloses crystal violet lactone, U.S. Pat. No. 3,681,390, issued Aug. 1, 1972, discloses aryl-substituted fluorans.

U.S. Pat. No. 3,672,935, issued June 27, 1972, discloses use of colorless chromogenic compounds in pressure-sensitive record material.

SUMMARY OF THE INVENTION

Colorable chromogenic compounds having at least one benzoindolyl moiety have been discovered which compounds are initially substantially colorless but produce dark-colored products on reaction with certain acid materials. The benzoindolyl-containing chromogenic compounds exhibit broad, flat, light absorption spectra, in the colored form, over the visible wavelengths. It is an object of this invention to provide such benzoindol-containing compounds and methods for making them.

An important use for the compounds of this invention resides in their incorporation into pressure-sensitive record systems as a colorable reactant for development of color on application of a mark-forming force. Hence, it is an object of this invention to provide substances having color response and chromogenic properties, which substances can be incorporated in a web or coated onto the surface of a web to provide a record sheet or a manifolding unit, and which are useful in carrying out methods of marking involving reactive contact with a color-activating material to develop dark-colored materials in areas where marking is desired.

It is an object of this invention to provide modified compounds, based upon the aforementioned benzoindolyl-containing compounds, which are substantially colorless, or slightly colored, offering a variety of chromogenic characteristics, and developing dark-colored substances having broad spectrum absorption upon contact with color-activating materials.

BRIEF DESCRIPTION OF THE DRAWING

The chromogenic compounds of this invention include a large variety of several moieties with the benzoindolyl moieties and lactone rings being necessarily common to all. In order to more completely and more distinctly disclose the variety of moiety combinations which forms a part of this invention, a drawing is included which is a schematic representation of the combinations, by structural formula.

The drawing represents a figurative, schematic, step-by-step structural development of the benzoindolyl-containing compounds of this invention, as they can be prepared. A dicarboxylic anhydride (I) is combined with a substrate reactant (A) to yield a keto acid (II), which is, in turn, combined with a benzoindolyl substrate reactant (B) to yield the chromogenic compound (III) of this invention. Alternatively, the anhydride (I) can be reacted directly with the benzoindolyl substrate to give a keto acid (II) which can then be further reacted with other substrates. The structural development shown is not necessarily a representation of the actual compound synthesis. The synthetic process is not embraced as a part of this invention.

The dicarboxylic anhydride (I) in the Figure includes E as the supporting molecular structure and E represents a large variety of structures including aromatic and heterocyclic, substituted and unsubstituted. The substitutions include halo, nitro, and alkyl and dialkyl-amino with alkyl of less than seven carbon atoms. Halogen or halo-, in this invention, means fluorine, chlorine, bromine and iodine. (I) is not required to be a dicarboxylic anhydride. A dicarboxylic acid will suffice if the keto acid-forming reaction is conducted under dehydrating conditions such as in acetic anhydride.

Figuratively speaking and in accord with the drawing, substrate moieties are added to the supporting molecular structure and at least one of the substrate moieties must be a benzoindolyl moiety. Substrate moieties are added at (A) to yield (II), a keto acid; and at (B) to yield (III), the compound of this invention.

DETAILED DESCRIPTION OF THE INVENTION

It should be remembered that what is considered to be an essential element of the invention herein is the presence of a benzoindolyl moiety in a colorless but colorable chromogenic material. At the present time, the chromogenic compounds of this invention enjoy extensive eligibility for use in pressure-sensitive and thermally-sensitive mark-forming systems. Pressure-sensitive mark-forming systems provide a marking system of disposing on and/or within sheet support material unreacted mark-forming components and a liquid solvent in which each of the mark-forming components is soluble, said liquid solvent being present in such form that it is maintained isolated by a pressure-rupturable barrier, from at least one of the mark-forming components until application of pressure causes a breach of the barrier in the area delineated by the pressure pattern. The mark-forming components are thereby brought into reactive contact, producing a distinctive mark.

The method of marking comprises providing a chromogenic compound selected from among the above-mentioned compounds and bringing such chromogenic compound into reactive contact, in areas where marking is desired, with an acidic color-activating substance to produce a dark-colored form of the chromogenic compound.

The acidic materials can be any compound within the definition of a Lewis acid, i.e., an electron acceptor. Preferably, acidic organic polymers such as phenolic polymers are employed as the acidic material. It is noted that the polymeric mark-forming components should have a common solubility with the chromogenic compound in at least one liquid solvent when the acid-reacting material is a phenolic or other organic acidic polymer. It is also noted that in a single system several chromogenic compounds can be used with the same or different polymeric materials. Several polymeric materials can be reactively contacted with a single chromogenic compound or with a mixture of chromogenic compounds.

The acidic polymeric material useful in this invention includes phenol polymers, phenol acetylene polymers, alkyl-phenolacetylene polymers, maleic acid-rosin resins, partially or wholly hydrolyzed styrene-maleic anhydride copolymers and ethylene-maleic anhydride copolymers, carboxy polymethylene and wholly or partially hydrolyzed vinyl methyl ether maleic anhydride copolymers and mixtures thereof.

When the acidic material is one of the aforementioned organic polymers, the liquid solvent chosen must be capable of dissolving the mark-forming components. The solvent can be volatile or non-volatile and a single or multiple component solvent may be used which is wholly or partially volatile. Examples of volatile solvents useful in the aforedescribed basic chromogen-acidic polymer are toluene, petroleum distillate, perchloroethylene, and xylene. Examples of non-volatile solvents are high-boiling point petroleum fractions, dioctyl adipate, biphenyls, diphenyl alkanes, and the like.

Generally, the solvent chosen should be capable of dissolving at least 0.3 percent, by weight, of the chromogenic compounds and at least about 3-5 percent, by weight, of the polymeric material. A further criterion of the solvent is that it must not interfere with the mark-forming reaction.

The support member on which the components of the system are disposed may comprise a single or dual sheet assembly. In the case where all components are disposed on a single sheet surface, the record material is referred to as a "self-contained" system. Where there must be a migration of the solvent, with or without mark-forming component, from one sheet to another, the record material is referred to as a "transfer" system. (Such a system can also be referred to as a "two-fold" system, in that at least two sheets are required and each sheet includes a component, or components, essential to the mark-forming reaction.) Where a copious amount of the colored reaction product in liquid form is produced on a surface of one sheet, it can produce a mark by transfer to a second sheet as a colored mark.

The polymeric material can be dissolved in ink composition vehicles to form a printing "ink" of colorless character and, thus, can be used to spot-print a proposed record sheet unit sensitized for recording in a reaction-produced color in those areas by application of a solution of the chromogenic material. In the case of phenolic polymer, a printing ink can be made of up to 75 percent, by weight, of the phenolic polymeric material in a petroleum solvent to a viscosity suitable for printing purposes.

In the mark-forming system herein, the acidic mark-forming components(s) reacts with the chromogenic materials(s) to effect distinctive color formation or color change. In a multi-sheet system in which an acid organic polymer is employed, it is desirable to include other materials to supplement the reactants. For example, kaolin can be added to improve the transfer of the liquid and/or the dissolved materials between the sheets. In addition, other materials such as bentonite, attapulgite, talc, feldspar, halloysite, magnesium trisilicate, silica gel, pyrophyllite, zinc sulfide, calcium sulfate, calcium citrate, calcium phosphate, calcium fluoride, barium sulfate, and tannic acid can be included. It should be noted that mineral materials such as kaolin, attapulgite, silica gel, silton clay, and the like can, also be used alone or in combination with other materials as an acidic material coreactant.

Various methods known to the prior art and disclosed in the aforementioned U.S. Pat. No. 3,672,935 can be employed in coating compositions of the mark-forming materials into their supporting sheets. An example of the compositions which can be coated onto the surface of an underlying sheet of a two-sheet system to react with the chromogenic material on the underside of any overlying sheet is as follows:

| Coating Composition | Percent by Weight |
| --- | --- |
| Phenolic polymer mixture | 17 |
| Paper coating kaolin (white) | 57 |
| Calcium carbonate | 12 |
| Styrene butadiene latex | 4 |
| Ethylated starch | 8 |
| Gum arabic | 2 |
| | 100 |

Thermally-sensitive mark-forming systems can also be prepared using the compounds of this invention.

The compounds of this invention can be prepared to be symmetrical or not as will be discussed in the examples which follow. Referring, again to the Figure;–E can be the following:

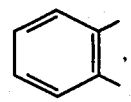

unsubstituted and alkyl-, chloro-, dichloro-, trichloro-, tetrachloro-, bromo-, dibromo-, tribromo-, tetrabromo-, nitro-, and dialkylamino-substituted;

A can be the following:

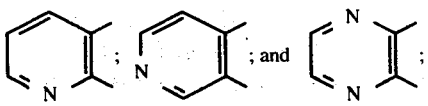

B can be the following:

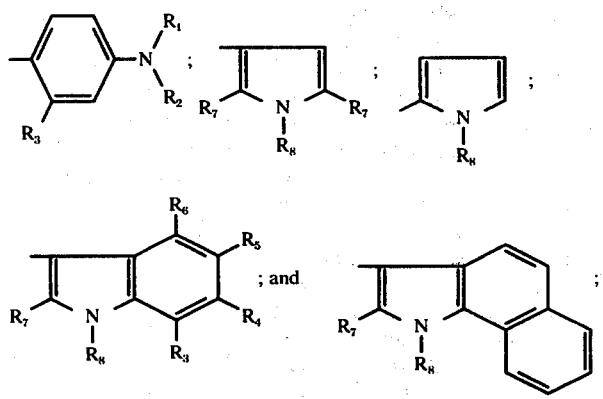

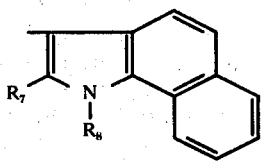

wherein $R_1$ and $R_2$ are hydrogen, alkyl, substituted phenyl, unsubstituted phenyl, benzyl, cycloalkyl, and acyl; $R_3$, $R_4$, $R_5$ and $R_6$ are hydrogen, alkyl, aryl, alkoxy, halo, aralkyl, dialkylamino, monoalkylamino, amino, acylamino, mercapto, and alkylthio; and $R_7$ and $R_8$ are hyrogen, phenyl and alkyl. $R_1$ and $R_2$ are not both phenyl.

It should be understood that "alkyl" and any group requiring alkyl, such as "alkoxy" or "dialkylamino" means methyl, ethyl, propyl (including isopropyl), butyl (including isobutyl and tert-butyl), pentyl (including all five-carbon isomers), hexyl (including all six-carbon isomers), and the like having less than seven carbon atoms.

This invention is further illustrated by the following examples. The reactants and the proportions and other specific conditions are represented as being typical and should not be construed to limit the invention.

DESCRIPTION OF THE PREFERRED EMBODIMENTS

In the following examples, general procedures for preparing certain compounds of this invention are disclosed; and the examples are followed by a listing of exemplary, additional, eligible components. The listing is not intended to be exhaustive and it must be remembered that the moieties, as previously defined, are all eligible for use in any combination in preparing the compounds.

PREPARATION OF 1-ETHYL-2-METHYL-1H-BENZ[G]INDOLE.

Although preparation of substituted benzoindole compounds is known, a method is provided herein to afford a more complete disclosure.

(a) A mixture of 52 grams of N-ethyl- α-naphthylamine, 14 grams of chloroacetone, and 40 milliliters of absolute ethanol are refluxed for 72 hours and then cooled. The reaction mixture is allowed to stand for several days and then precipitated N-ethyl- α-naphthylamine hydrochloride is separated by filtration. Hydrochloric acid is added to the filtrate and the filtrate is extracted with ether. The ether is dried with sodium sulfate and evaporated to leave an oily residue which distilled at 139°–150° under 0.05 tor of pressure. About 10 grams of 1-ethyl-3-methyl-1H-benz[g]indole was recovered having a melting point of 48–49° C.

(b) Four hundred grams of phosphorous pentoxide ($P_2O_5$) are heated with 200 milliliters of 85 weight percent phosphoric acid at about 220° C. until it is nearly dissolved. The mixture is cooled to about 160° C. and about 25 grams of 1-ethyl-3-methyl-1H-benz[-g]indole are added and stirred for about twelve hours while maintaining the heat. The mixture is cooled to about 65° C., poured into ice water, and then heated to dissolve the resulting gummy material. On cooling, an oil separates and solidifies on the surface. The separated solid is removed by filtration and is then dissolved in chloroform with magnesium sulfate as a drying agent. The solution is filtered, the chloroform is evaporated, and the residue is distilled at 139°–154° C. under 0.5 tor pressure. About 19 grams of 1-ethyl-2-methyl-1H-benz[g]indole was recovered having a melting point of 73°–75° C.

Other benzoindole compounds are made by the above procedure wherein the indolyl substitutions are hydrogen, phenyl and other alkyl.

EXAMPLE 1

Preparation of 3-(1-ethyl-2-methylindol-3-yl)-3-(1-ethyl-2-methyl-1H-benz[g]indol-3-yl)phthalide.

With reference to the drawing in respect of this example and like examples which follow, the description of compound preparation commences at (II), the keto-acid, because preparation of the keto-acid is known or not difficult. For instance, the keto-acid of this example is easily prepared, by mol-for-mol combination of phthalic anhydride (I) and 1-ethyl-2-methylindol-3-yl (A) in a solvent such as methylene chloride.

For ease in understanding, the Examples are summarized in listings of components, the (A) components are listed as radicals, and the (B) components are listed as compounds. Such listing is believed to facilitate comprehension of the molecular structures.

Combining the appropriate keto-acid, 1-ethyl-2-methyl-3-(2-carboxybenzoyl)indole (II), with an appropriate benzoindole (B), results in a compound of this invention. A solution of 2.1 grams of 1-ethyl-2-methyl-1H-benz[g]indole and 3.0 grams of the keto-acid in 35 milliliters of acetic anhydride is stirred for about two hours with gradual heating to about 85° C. The solution is poured into icy ammonia water and is extracted with toluene. The toluene is dried and evaporated and 4.5 grams of the title compound is obtained. The title compound is purified by recrystallization from toluene-petroleum ether to a melting point of 177.5°–178.0° C. A solution of the product imparts a red color to paper coated with a phenolic resin or silton clay or a combination of the two.

This example is also conducted using disubstituted amino phenyl moieties such as, diethylaminophenyl and 2-ethoxy-4-di-tert-butylaminophenyl, and other indolyl moieties such as, 1-phenyl-2-propylindolyl and 2-phenylindolyl. Benzoindolyl moieties, such as, 1-phenyl-2-propylbenzoindolyl and 2-phenylbenzoindolyl are also used.

This example is also conducted using other anhydrides such as 3 and 4-nitro phthalic anhydride and 4-dihexyl phthalic anhydride.

Example 1, Summarized (I) phthalic anhydride
(A) 1-ethyl-2-methylindolyl
(B) 1-ethyl-2-methyl-1H-benz[g]indole also
(B) 1-hexyl-1H-benz[g]indole also
(B) 1-phenyl-2-butyl-1H-benz[g]indole also
(A) 1-phenylindolyl also (A) 2-phenylindolyl

EXAMPLE 2

Preparation of 3-(p-diethylaminophenyl)-3-(1-ethyl-2-methyl-1H-benz[g]indol-3-yl)phthalide.

The keto-acid in this example is prepared by mol-for-mol combination of phthalic anhydride (I) and N,N-diethylaniline (A) in a solvent such as methylene chloride and, if required, in the presence of aluminum chloride or other Friedel-Crafts catalysts.

The keto-acid and benzoindole are reacted in amounts and under conditions as disclosed in Example 1, above.

The product exhibits a melting point of 195°–196° C. and a solution of the product imparts a blue-purple color to paper coated with a phenolic resin or silton clay or a combination of the two. The calculated analysis for $C_{33}H_{32}N_2O_2$, the title compound, is C, 81.12%; H, 6.60%; and N, 5.73%. Found, on analysis: C, 81.25%; H, 6.54%; and N, 5.79%.

This example is also conducted using 1-hexyl-1H-benz[g]indole, 1-phenyl-2-butyl-1H-benz[g]indole, 2-phenyl-1H-benz[g]indole, and the like.

Example 2, Summarized (I) phthalic anhydride
(A) p-diethylaminophenyl
(B) 1-ethyl-2-methyl-1H-benz[g]indole

EXAMPLE 3

Preparation of 3-(p-dimethylaminophenyl)-3-(1-ethyl-2-methyl-1H-benz[g]indole-3-yl)-5-dimethylaminophthalide.

A solution of about 3.5 grams of 4,4'-tetramethylamino-2'-carboxybenzophenone and 2.2 grams of 1-ethyl-2-methyl-1H-benz[g]indole in 100 milliliters of acetic anhydride is heated and stirred at about 80°–90° C. of for 3 hours. The solution is isolated and purified as previously described. 3.2 grams of the title compound is obtained having a melting point of 249°–251° C. A solution of the product imparts a purple color to paper coated with a phenolic resin or silton clay or a combination of the two. The calculated analysis for $C_{33}H_{33}N_3O_2$, the title compound, is C, 78.70%; H, 6.60%; and N, 8.34%. Found, on analysis: C, 78.72%; H, 6.56%; and N, 8.34%.

Example 3, Summarized

I. p-dimethylaminophthalic anhydride
A. p-dimethylaminophenyl
B. 1-ethyl-2-methyl-1H-benz[g]indole Also used as (I) are p-di-t-butylamino phthalic anhydride, p-dihexylaminophthalic anhyride, 3-propyl-5-methylphthalic anhydride, and the like.

EXAMPLE 4

Preparation of 3-(p-diethylaminophenyl)-3-(1-ethyl-2-methyl-1H-benz[g]indol-3-yl)-4,5,6,7-tetrachlorophthalide.

A solution of about 6.5 grams of 3,4,5,6-tetrachloro-2-carboxy-4'-diethylaminobenzophenone and about 3.1 grams of 1-ethyl-2-methyl-1H-benz[g]indole in 50 milliliters of acetic anhydride is refluxed for about one hour and then cooled. That reaction mixture is poured over ice and ammonia, extracted twice with a 1:1 toluene-chloroform mixture and dried using sodium sulfate. The solution is concentrated by evaporation of the solvent and the title compound is crystallized by washing with petroleum ether. 9.3 grams of the title compound is obtained having a melting point of 232°–235° C. A solution of product imparts a blue color to paper coated with a phenolic resin or silton clay or a combination of the two. The calculated analysis for $C_{33}H_{28}N_2O_2Cl_4$, the title compound, is C, 63.28%; H, 4.51%; N, 4.57%; and Cl, 22.64%. Found, on analysis: C, 63.37%; H, 4.42%; N, 4.54%; an Cl, 22.49%.

This example is also conducted using 1-methyl-2-hexyl-1H-benz[g]indole, 1H-benz[g]indole, and the like.

Example 4, Summarized

I. 3,4,5,6-tetrachlorophthalic anhydride
A. p-diethylaminophenyl
B. 1-ethyl-2-methyl-1H-benz[g]indole Also used as (I) are mono-, di-, and trichlorophthalic anhydride and mono-, di-, tri-, and tetrabromophthalic anhydride, and the like.

EXAMPLE 5

Preparation of 3-(1-ethyl-2-methylindol-3-yl)-3-(1-ethyl-2-methyl-1H-benz[g]indol-3-yl)-4,5,6,7-tetrachlorophthalide.

A solution of about 4.5 grams of 1-ethyl-2-methyl-3-(2-carboxy-3,4,5,6-tetrachlorobenzoyl)indole and about 3.2 grams of 1-ethyl-2-methyl-1H-benz[g]indole in 50 milliliters of acetic anhydride is heated at 90° C. for about four hours. The product is isolated as disclosed previously. 2.0 grams of the title compound is obtained having a melting point of 170°–177° C. A solution of the product imparts a purple color to paper coated with a phenolic resin or silton clay or a combination of the two. The calculated analysis for $C_{34}H_{26}N_2Cl_4O_2$, the title compound, is C, 64.17%; H, 4.12%; N, 4.40%; and Cl, 22.28%. Found, on analysis: C, 64.33%; H, 4.19%; N, 4.49%; Cl, 22.37%.

The title compound is also made as follows. A solution of about 4.4 grams of 3-(1-ethyl-2-methylindol-3-yl)-3-aceto-5,6,7,8-tetrachlorophthalide and about 2.1 grams of 1-ethyl-2-methyl-1H-benz[g]indole in 50 milliliters of methylene chloride is stirred for about 16 hours at about 20° C., with about 1.3 grams of aluminum chloride. The reaction mixture is poured into ice and hydrochloric acid and ammonia is added. The system is extracted with toluene. The toluene is washed with water and is then evaporated to yield about 2.7 grams of the title compound.

Example 5, Summarized
 I. 3,4,5,6-tetrachlorophthalic anhydride
  A. 1-ethyl-2-methylindol-3-yl
  B. 1-ethyl-2-methyl-1H-benz[g]indole

EXAMPLE 6

Preparation of 7-(1-ethyl-2-methyl-1H-benz[g]indole-3-yl)-7-(1-ethyl-2-methylindol-3-yl)-5,7-dihydrofuro[3,4-b]-pyridin-7-one.

A solution of about 2.0 grams of (1-ethyl-2-methylindol-3-yl)-(2-carboxypyridin-3-yl)ketone and about 2.0 grams of 1-ethyl-2-methyl-1H-benz[g]indole is stirred and heated at 85° C. for about four hours. The reaction mixture is extracted with toluene and the title compound is isolated, as previously described. 2.9 grams of the title compound is obtained having a melting point of 160°–164° C. A solution of the product imparts a reddish-purple color to paper coated with a phenolic resin or silton clay or a combination of the two.

A chromogenic material di-substituted with benzoindole is prepared by using a benzoindole keto-acid. To modify the above example, (1-ethyl-2-methyl-1H-benz[g]indol-3-yl)-(2-carboxypyridin-3-yl)ketone is substituted for that keto-acid and the resulting compound is bis-7,7-(1-ethyl-2-methyl-1H-benz[g]indol-3-yl)-5,7-dihydrofuro[3,4-b]-pyridin-7-one. A solution of this product imparts a blue color to paper coated with a phenolic resin or silton clay or a combination of the two.

EXAMPLE 7

Preparation of 7-(1-ethyl-2-methyl-1H-benz[g]indol-3-yl)-7-(1-dimethylamino-3-methylphen-4-yl)-5,7-dihydrofuro[3,4-b]pyrazin-7-one.

(a) The appropriate keto-acid is prepared as follows. A mixture of about 6 grams of 2,3-pyrazinedicarboxylic anhydride and about 10.5 grams of 1-ethyl-2-methyl-1H-benz[g]indole is heated on a steam bath for about 24 hours. The mixture is extracted with toluene. About 2 grams of (1-ethyl-2-methylindol-3-yl)-(2-carboxypyrazin-3-yl)ketone is obtained having a melting point of 212°–213° C.

(b) A solution of 2.0 grams of the above-prepared keto-acid and 1.6 grams of N,N-diethyl-m-toluidine and refluxed in acetic anhydride for one minute. The reaction mixture is cooled and basified with ammonia, and the title compound is extracted using toluene.

A solution of the product imparts a blue color to paper coated with a phenolic resin or silton clay or a combination of the two.

Example 7, Summarized
 I. 2,3-pyrazinedicarboxylic acid anhydride
  A. 2-methyl-4-diethylaminophenyl
  B. 1-ethyl-2-methyl-1H-benz[g]indole This example is also conducted using the following as (A) moieties: 2-methyl-4-diethylaminophenyl; 2-methyl-4-(ethylbenzyl)-aminophenyl; 2-ethoxy-4-diethylaminophenyl; p-(ethylbenzyl)aminophenyl; and 1-ethyl-2-methylbenzoindol-3-yl, all of which imparts a blue color to paper coated with a phenolic resin or silton clay or a combination of the two.

EXAMPLE 8

Preparation of 7-(1-ethyl-2-methyl-1H-benz[g]indol-3-yl)-7-(1,2,5-trimethylpyrrol-3-yl)-5,7-dihydrofuro[3,4-b]pyrazin-7-one A solution of the keto-acid of Example 7(a) is refluxed with 1,2,5-trimethylpyrrole for a minute or two and the title product is isolated, as previously described. A solution of the product imparts a red color to paper coated with a phenolic resin or silton clay or a combination of the two.

When 1-phenyl-2,5-dimethylpyrrole is used, the reaction product is 7-(1-ethyl-2-methyl-1H-benz[g]indol-3-yl)-7-(1-phenyl-2,5-dimethylpyrrol-3-yl)-5,7-dihydrofuro[3,4-b]pyrazin-7-one which yields an orange color.

When 1-methylpyrrole is used, the reaction product is 7-(1-ethyl-2-methyl-1H-benz[g]indol-3-yl)-7-(1-methylpyrrol-2-yl)-5.7-dihydrofuro[3,4-b]pyrazin-7-one which yields a purple color.

When 1-phenylpyrrole is used, the reaction product is 7-(1-ethyl-2-methyl-1H-benz[g]indol-3-yl)-7-(1-phenylpyrrol-2-yl)-5,7-dihydorfuro[3,4-b]pyrazin-7-one which yields a purple color.

Example 8, Summarized.
 I. 2,3-pyrazinedicarboxylic acid anhydride
  A. 1,2,5-trimethylpyrrolyl
  A. 1-phenyl-2,5-dimethylpyrrolyl
  A. 1-methylpyrrolyl
  A. 1-phenylpyrrolyl
  B. 1-ethyl-2-methyl-1H-benz[g]indole Other moieties, used as (A) in all of the above examples, include:
2-methoxy-4-diethylaminophenyl;
2-butoxy-4-diethylaminophenyl;
2-methoxy-4-cyclohexylaminophenyl;
phenylaminophenyl;
benzylaminophenyl;
aminophenyl;
2-hexyl-4-dihexylaminophenyl;
2-chloro-4-diethylaminophenyl;
2-phenyl-4-dimethylaminophenyl;
2-dimethylamino-4-diethylaminophenyl;
2-butylamino-4-dimethylaminophenyl;
2-amino-4-dimethylaminophenyl;
2-acetamino-4-dimethylaminophenyl;
2-bromo-4-dimethylaminophenyl;
2-ethoxy-4-dimethylaminophenyl;

2-hexoxy-4-dimethylaminophenyl;
1-phenyl-2-methylindolyl;
1-ethyl-2-methyl-5-hexoxyindolyl;
1-hexyl-2-ethylindolyl;
1-ethyl-2-methyl-1H-benz[g]indolyl and the like.

What is claimed is:

1. A compound represented by the formula:

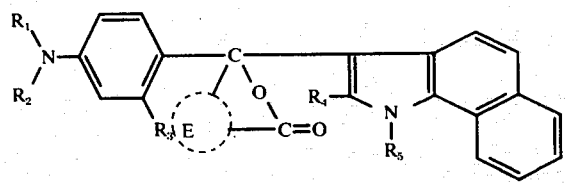

wherein E is:

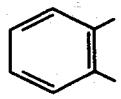

unsubstituted and alkyl-, chloro-, dichloro-, trichloro-, tetrachloro-, bromo-, dibromo-, tribromo-, tetrabromo-, nitro-, and dialkylaminosubstituted;

$R_1$ and $R_2$ are: hyrogen, alkyl, phenyl, benzyl, and cyclohexyl but $R_1$ and $R_2$ are not both phenyl;

$R_3$ is: hydrogen, alkyl, phenyl, alkoxy, halo, dialkylamino, monoalkylamino, amino an acetylamino; and $R_4$ and R are: hydrogen, phenyl and alkyl wherein alkyl, all occurrences, and alkoxy have 1 to 6 carbon atoms.

2. The compound of claim 1 wherein E is

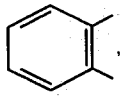

unsubstituted.

3. The compound of claim 1 wherein E is

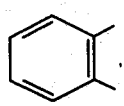

tetrachlorinated.

4. The compound of claim 1 wherein $R_4$ and $R_5$ are alkyl.

* * * * *

UNITED STATES PATENT AND TRADEMARK OFFICE
CERTIFICATE OF CORRECTION

PATENT NO. : 4,016,174
DATED : April 5, 1977
INVENTOR(S) : Sheldon Farber

It is certified that error appears in the above-identified patent and that said Letters Patent are hereby corrected as shown below:

Col. 9, line 55, the "m" in "(1-dime-" has been deleted.

Claim 1, col. 11, lines 15 and 16, "  "

has been changed to --- 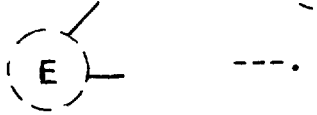 ---.

Claim 1, col. 12, line 7, "an" has been changed to --- and ---.

Claim 1, col. 12, line 9, "Rare" has been changed to --- $R_5$ are ---.

Signed and Sealed this

Twenty-ninth Day of November 19

[SEAL]

Attest:

RUTH C. MASON
Attesting Officer

LUTRELLE F. PARKER
Acting Commissioner of Patents and Trademarks